(12) United States Patent
Kameshima et al.

(10) Patent No.: US 9,241,116 B2
(45) Date of Patent: Jan. 19, 2016

(54) METHOD FOR CONTROLLING RADIATION IMAGE PICKUP APPARATUS, RADIATION IMAGE PICKUP APPARATUS, AND RADIATION IMAGE PICKUP SYSTEM

(71) Applicant: CANON KABUSHIKI KAISHA, Tokyo (JP)

(72) Inventors: Toshio Kameshima, Kumagaya (JP); Tomoyuki Yagi, Honjo (JP); Katsuro Takenaka, Honjo (JP); Sho Sato, Saitama (JP); Atsushi Iwashita, Honjo (JP); Eriko Sugawara, Honjo (JP); Hideyuki Okada, Honjo (JP)

(73) Assignee: Canon Kabushiki Kaisha, Tokyo (JP)

( * ) Notice: Subject to any disclaimer, the term of this patent is extended or adjusted under 35 U.S.C. 154(b) by 251 days.

(21) Appl. No.: 13/934,767

(22) Filed: Jul. 3, 2013

(65) Prior Publication Data

US 2014/0008519 A1 Jan. 9, 2014

(30) Foreign Application Priority Data

Jul. 6, 2012 (JP) ................................. 2012-152393

(51) Int. Cl.
*H01L 27/00* (2006.01)
*G01T 1/17* (2006.01)
*H04N 5/341* (2011.01)
*H04N 5/32* (2006.01)
*H04N 5/361* (2011.01)
*A61B 6/00* (2006.01)

(52) U.S. Cl.
CPC ........ *H04N 5/341* (2013.01); *G01T 1/17* (2013.01); *H04N 5/32* (2013.01); *H04N 5/361* (2013.01); *A61B 6/4258* (2013.01)

(58) Field of Classification Search
CPC .................................... G01T 1/16; G01T 1/17
USPC ............. 250/208.1, 393, 394, 370.09; 378/91
See application file for complete search history.

(56) References Cited

U.S. PATENT DOCUMENTS

2003/0086523 A1 * 5/2003 Tashiro et al. .................. 378/19
2007/0125952 A1   6/2007 Endo et al.

FOREIGN PATENT DOCUMENTS

JP 2011185622 A 9/2011

* cited by examiner

*Primary Examiner* — Kevin Pyo
(74) *Attorney, Agent, or Firm* — Canon USA Inc. IP Division

(57) ABSTRACT

A radiation image pickup apparatus capable of setting an optimum threshold value used for instantaneously and highly accurately detecting the presence/absence of irradiation includes a pixel array having a plurality of pixels arranged in a matrix, where each of the pixels includes a conversion element and a switch element, a drive circuit for supplying a drive signal for controlling the switch element between a conducting state and a non-conducting state, a detection unit for outputting a detection signal varying with the intensity of irradiation of the pixel array, and an arithmetic unit for calculating an end threshold value used to detect end of irradiation on the basis of the signal output from the detection unit during a period of time during which irradiation is applied to the pixel array in which the switch elements of the pixels are set in a non-conducting state by the drive circuit.

20 Claims, 11 Drawing Sheets

FIG. 3B

| | TUBE VOLTAGE [kVp] | TUBE CURRENT [mA] | IRRADIATION TIME [ms] | DISTANCE [cm] | DIAPHRAGM | FILTER | END THRESHOLD VALUE | DELAY TIME | START THRESHOLD VALUE |
|---|---|---|---|---|---|---|---|---|---|
| CONDITION 1 | 50 | 125 | 50 | 100 | CHEST USE | YES | Sth1 | DT1 | Sth' |
| CONDITION 2 | 50 | 125 | 50 | 100 | CHEST USE | NO | Sth2 | DT2 | Sth' |
| CONDITION 3 | 50 | 125 | 50 | 100 | ABDOMEN USE | YES | Sth3 | DT3 | Sth' |
| CONDITION 4 | 50 | 125 | 50 | 100 | ABDOMEN USE | NO | Sth4 | DT4 | Sth' |
| CONDITION 5 | 50 | 125 | 50 | 100 | HEAD USE | YES | Sth5 | DT5 | Sth' |
| CONDITION 6 | 50 | 125 | 50 | 100 | HEAD USE | NO | Sth6 | DT6 | Sth' |
| CONDITION 7 | 50 | 125 | 50 | 120 | CHEST USE | YES | Sth7 | DT7 | Sth' |
| CONDITION 8 | 50 | 125 | 50 | 120 | CHEST USE | NO | Sth8 | DT8 | Sth' |
| ... | ... | ... | ... | ... | ... | ... | ... | ... | ... |
| CONDITION 12 | 50 | 125 | 50 | 120 | HEAD USE | NO | Sth12 | DT12 | Sth' |
| CONDITION 13 | 50 | 125 | 50 | 140 | CHEST USE | YES | Sth13 | DT13 | Sth' |
| ... | ... | ... | ... | ... | ... | ... | ... | ... | ... |
| CONDITION 36 | 50 | 125 | 50 | 200 | HEAD USE | NO | Sth36 | DT36 | Sth' |
| CONDITION 37 | 80 | 63 | 50 | 100 | CHEST USE | YES | Sth37 | DT37 | Sth' |
| ... | ... | ... | ... | ... | ... | ... | ... | ... | ... |
| CONDITION 72 | 80 | 63 | 50 | 200 | HEAD USE | NO | Sth72 | DT72 | Sth' |
| CONDITION 73 | 140 | 40 | 50 | 100 | CHEST USE | YES | Sth73 | DT73 | Sth' |
| ... | ... | ... | ... | ... | ... | ... | ... | ... | ... |
| CONDITION 108 | 140 | 40 | 50 | 200 | HEAD USE | NO | Sth108 | DT108 | Sth' |

METHOD FOR CONTROLLING RADIATION IMAGE PICKUP APPARATUS, RADIATION IMAGE PICKUP APPARATUS, AND RADIATION IMAGE PICKUP SYSTEM

BACKGROUND OF THE INVENTION

1. Field of the Invention

The present invention relates to a method for controlling a radiation image pickup apparatus suitable for medical diagnosis and industrial non-destructive inspection, the radiation image pickup apparatus, and a radiation image pickup system and, in particular, to a method for controlling a radiation image pickup apparatus, the radiation image pickup apparatus, and a radiation image pickup system capable of detecting the presence of irradiation, such as start and end of irradiation.

2. Description of the Related Art

A radiation image pickup apparatus including a flat panel detector (hereinafter simply referred to as an "FPD") performs an image capturing operation in synchronization with irradiation performed by a radiation generating apparatus. To synchronize two operations, the following techniques are employed. That is, as described in U.S. patent application Ser. No. 2007/0125952, a radiation image pickup apparatus includes a plurality of pixels. Each of the pixels includes a conversion element that converts radiation or light into electric carriers and a switch element that transfers an electric signal based on the electric carriers so as to be capable of providing a desired voltage to one of two electrodes of the conversion element. The pixel further includes a detection unit for detecting the presence of irradiation. Before the detection unit detects irradiation from the radiation generating apparatus, a conducting voltage is sequentially provided from a drive circuit to the switch elements on a row-by-row basis in order to switch the switch elements to a conducting state. In this manner, the voltage of one of the electrodes of the conversion element is reset. Thereafter, if the detection unit detects start of irradiation from the radiation generating apparatus, supply of the conducting voltage from the drive circuit is stopped. Thus, a non-conducting voltage is supplied from the drive circuit to all of the switch elements in order to switch the switch elements to a non-conducting state. Accordingly, the electric carriers generated in the conversion element is accumulated in each of the pixels. In contrast, if the detection unit detects end of irradiation, a conducting voltage is sequentially supplied from the drive circuit to the switch elements on a row-by-row basis. Thus, an electric signal in accordance with the accumulated electric carriers is transferred from the pixel.

Japanese Patent Laid-Open No. 2011-185622 describes that a noise component that is not caused by irradiation is coupled with a signal output from a detection unit for detecting irradiation due to a reset operation, and the noise component has a particular variation. Therefore, according to Japanese Patent Laid-Open No. 2011-185622, the profile of a signal used for detecting irradiation is measured in advance, and differential processing is performed on a measured signal for detecting irradiation using the profile. Thereafter, the signal subjected to the differential processing is compared with a predetermined threshold value to detect start of irradiation.

As described above, in order to accurately detect the presence/absence of irradiation, the threshold value needs to be optimally set. However, U.S. patent application Ser. No. 2007/0125952 and Japanese Patent Laid-Open No. 2011-185622 do not mention the setting of an optimal threshold value and, thus, further study is needed.

Accordingly, the present invention provides a radiation image pickup apparatus capable of setting an optimal threshold value used for instantaneously and highly accurately detecting the presence/absence of irradiation.

SUMMARY OF THE INVENTION

According to an embodiment of the present invention, a method for controlling a radiation image pickup apparatus is provided. The radiation image pickup apparatus includes a pixel array having a plurality of pixels arranged in a matrix, a drive circuit, a readout circuit, and a detection unit. Each of the pixels includes a conversion element and a switch element and converts radiation into an electric signal. The drive circuit supplies, to each of the switch elements of the pixels, a drive signal for controlling the switch element between a conducting state and a non-conducting state. The readout circuit reads an image signal based on the electric signal. The detection unit outputting a detection signal varying with the intensity of irradiation of the pixel array in order to detect irradiation of the pixel array. The method includes switching the radiation image pickup apparatus between a first mode and a second mode. In the first mode, an end threshold value used for detecting end of irradiation of the pixel array is calculated on the basis of the detection signal output from the detection unit during a period of time during which irradiation is applied to the pixel array in which the switch elements of the plurality of pixels are set in the non-conducting state by the drive circuit. In the second mode, a value of the detection signal output from the detection unit during a period of time during which irradiation is applied to the pixel array in which the switch elements of the pixels are set in the non-conducting state by the drive circuit is compared with the end threshold value. If the value of the detection signal is lower than the end threshold value after the first mode occurs, the switch elements of the plurality of pixels are sequentially set in the conducting state on a row-by-row basis by the drive circuit to transfer the electric signal. The readout circuit reads the image signal based on the transferred electric signal.

According to another embodiment of the present invention, a radiation image pickup apparatus includes a pixel array having a plurality of pixels arranged in a matrix, where each of the pixels includes a conversion element and a switch element and converts radiation emitted from a radiation generating apparatus into an electric signal, a drive circuit configured to supply a drive signal to each of the switch elements of the pixels so as to control the switch element between a conducting state and a non-conducting state, a detection unit configured to output a detection signal varying with an intensity of irradiation of the pixel array in order to detect irradiation of the pixel array, and an arithmetic unit configured to perform arithmetic operation processing to calculate an end threshold value used for detecting end of irradiation on the basis of the detection signal output from the detection unit during a period of time during which irradiation is applied to the pixel array in which the switch elements of the plurality of pixels are set in a non-conducting state by the drive circuit.

According to the present invention, a radiation image pickup apparatus capable of setting an optimum threshold value used for instantaneously and highly accurately detecting the presence/absence of irradiation can be provided.

Further features of the present invention will become apparent from the following description of exemplary embodiments with reference to the attached drawings.

BRIEF DESCRIPTION OF THE DRAWINGS

FIG. 3B illustrates a table containing the threshold values, each corresponding to one of a variety of conditions, stored in a storage unit.

DESCRIPTION OF THE EMBODIMENTS

Exemplary embodiments of the present invention are described in detail below with reference to the accompanying drawings. As used herein, the term "radiation" refers to an α beam, a β beam, or a γ beam, which is formed from particles (including photons) emitted by radioactive decay, and a beam having substantially the same energy as the beam or higher, such as an X-ray, a corpuscular ray, or a cosmic ray.

First Exemplary Embodiment

Figure 1A:
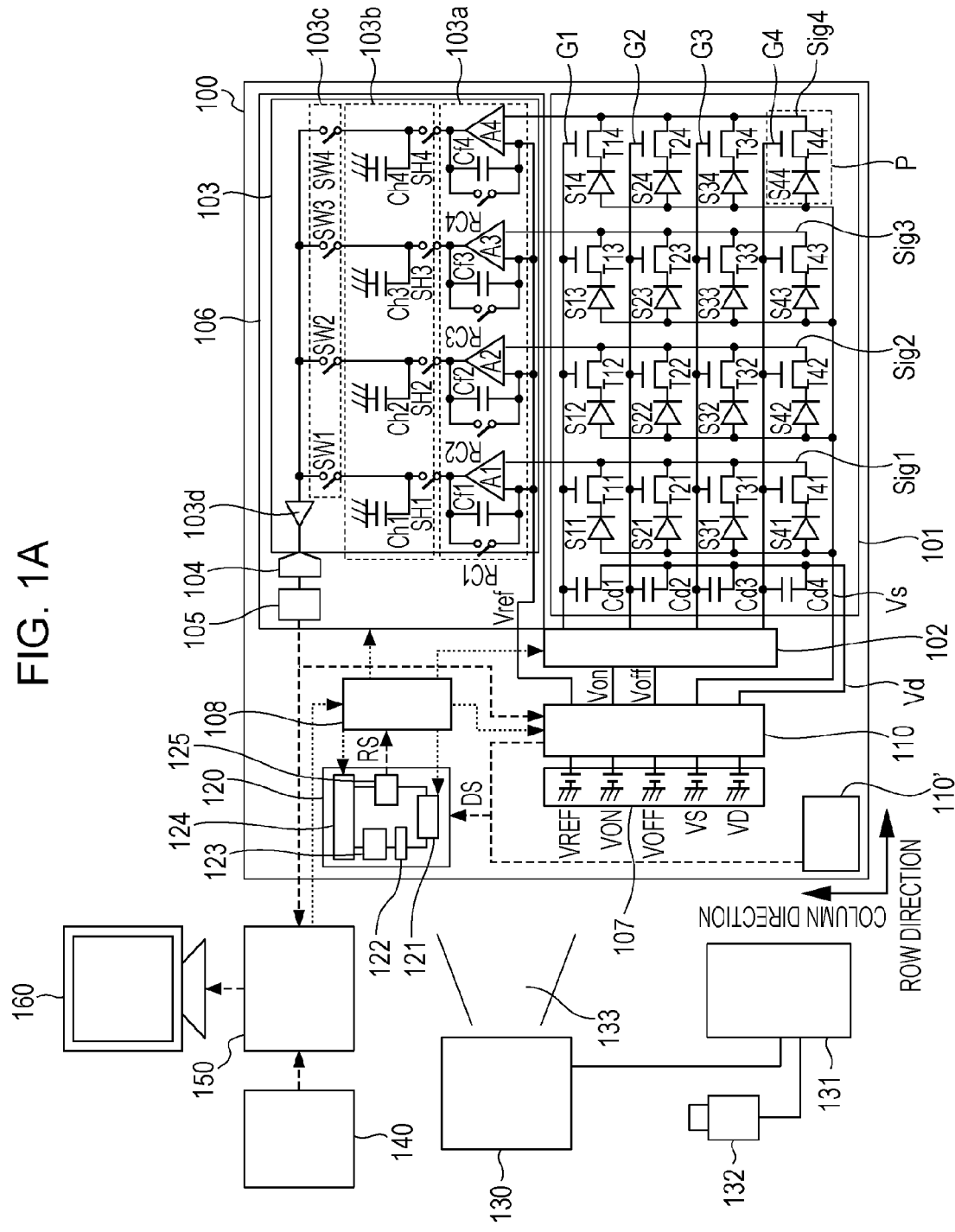
FIG. 1A is a schematic equivalent circuit diagram illustrating a radiation image pickup apparatus and a radiation image pickup system.

A radiation image pickup system and a radiation image pickup apparatus are described first with reference to FIG. 1A. FIG. 1A is a schematic equivalent circuit diagram illustrating the radiation image pickup apparatus and the radiation image pickup system.

The radiation image pickup system includes a radiation image pickup apparatus 100, a radiation generating apparatus 130, a radiation control apparatus 131, and an exposure button 132. Upon receiving a control signal from the exposure button 132, the radiation control apparatus 131 sends a control signal to the radiation generating apparatus 130. Thus, the radiation generating apparatus 130 performs control of emitting radiation 133. The radiation generating apparatus 130 can emit the radiation 133 under a plurality of irradiation conditions. The plurality of radiation conditions can be set using the radiation control apparatus 131. The radiation control apparatus 131 controls the radiation generating apparatus 130 in accordance with the preset irradiation condition. Examples of the irradiation condition include a tube voltage, a tube current, an irradiation time, a distance between the radiation generating apparatus 130 and the radiation image pickup apparatus 100, the state of a diaphragm of the radiation generating apparatus 130, and the presence/absence of a filter that controls the transparent wavelength for radiation. The radiation image pickup apparatus 100 includes a pixel array 101, a drive circuit 102, and a detection unit. The pixel array 101 includes a plurality of pixels P arranged in a matrix. Each of the pixels P includes a conversion element S and a switch element T and converts radiation into an electric signal. The conversion element S converts radiation that has been emitted from the radiation generating apparatus 130 and that has passed through a subject (not illustrated) into electric carriers. The conversion element S has a semiconductor layer between two electrodes. An indirect type conversion element or a direct type conversion element is suitably employed as the conversion element S. The indirect type conversion element includes a photoelectric conversion element and a wavelength conversion element that converts radiation into light in a wavelength range detectable by the photoelectric conversion element. The direct type conversion element directly converts radiation into electric carriers. Note that according to the present exemplary embodiment, a PIN photodiode that is disposed on an insulating substrate, such as a glass substrate, and that contains amorphous silicon as a main component is used as a photodiode serving as the photoelectric conversion element. The switch element T transfers the electric carriers of the conversion element S or an electric signal based on the electric carriers. A transistor including a control terminal and two main terminals is suitably employed as the switch element T. According to the present exemplary embodiment, a thin film transistor (TFT) is used as the switch element T. Note that according to the present exemplary embodiment, for simplicity, the pixel array 101 includes 4-by-4 pixels P. For example, a shift register is used as the drive circuit 102 that drives the pixel array 101. The drive circuit 102 supplies, to the switch element T of each of the pixels P, a drive signal that controls switching between the conducting state and the non-conducting state of the switch element T. The detection unit detects irradiation of the pixel array 101 by outputting the detection signal DS that varies with the intensity of irradiation of the pixel array 101. The detection unit includes at least one of a detection circuit 110 and a detection element 110'. The value of the detection signal DS varies with the presence/absence of irradiation, the intensity of radiation and the operation performed by the pixel array 101. The detection unit is described in more detail below.

As described in the related art, until start of emission of the radiation 133 from the radiation generating apparatus 130 is detected, the drive circuit 102 sequentially supplies a conducting voltage to the switch elements T of each of the rows to set the switch elements T in the conducting state. In this manner, the voltage of one of the electrodes of the conversion element S is initialized. Thereafter, when start of the emission of the radiation 133 from the radiation generating apparatus 130 is detected, supply of the conducting voltage from the drive circuit 102 is stopped. In this manner, the non-conducting voltage is supplied from the drive circuit 102 to all of the switch elements T to set the switch elements T in the non-conducting state. Thus, the electric carriers generated in the conversion element S are accumulated in each of the pixels P. In addition, if completion of emission of the radiation 133 is detected, the drive circuit 102 sequentially supplies a conducting voltage to the switch element T on a row-by-row basis and transfers an electric signal based on the accumulated electric carriers from the pixel P.

Figure 1B:
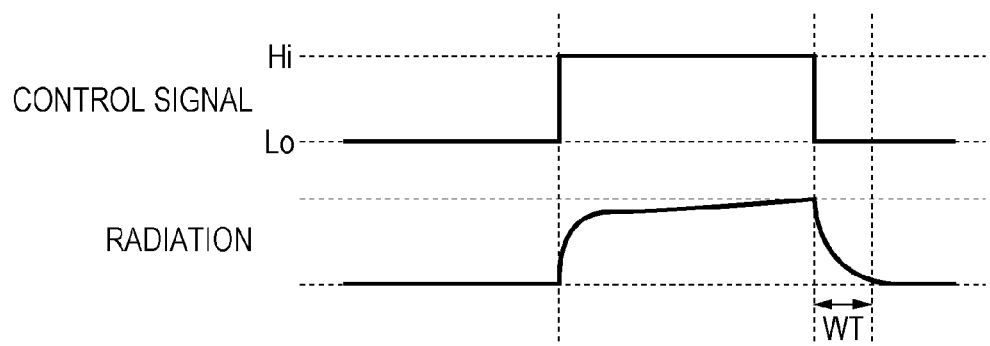
FIG. 1B is a timing diagram illustrating irradiation.

The control signal output from the radiation control apparatus 131 and the radiation 133 emitted from the radiation generating apparatus 130 are described below with reference to FIG. 1B. When the control signal output from the radiation control apparatus 131 is set in a Hi mode, supply of a desired tube voltage to the radiation generating apparatus 130 is started and, thus, emission of the radiation 133 is started. In contrast, when the control signal is set in a Lo mode, supply of the desired tube voltage to the radiation generating apparatus 130 is stopped and, thus, emission of the radiation 133 is completed. As illustrated in FIG. 1B, the intensity of the emitted radiation 133 is delayed behind switching of the control signal. In particular, "wave tails" which are delays occurring when the control signal is switched from Hi to Lo and which are indicated by "WT" in FIG. 1B need to be taken into account. If the switch element T is set in a conducting state and, thus, an electric signal is transmitted without taking into account the effect of a wave tail, radiation or light is emitted to the switch elements T of some of the pixels, and the radiation or light is not emitted to the other switch elements T. At that time, the switch elements T may be set in a conductive state. In such a case, the switch element T to which radiation or light is emitted and the switch element T to which radiation or light is not emitted have different transfer abilities. Accordingly, uneven signal transfer occurs in the switch elements T of the pixel array 101 and may have a negative effect on an image signal obtained.

Therefore, according to the present exemplary embodiment, the radiation image pickup apparatus 100 includes an arithmetic unit 120 for computing a threshold value Sth used to detect end of emission of the radiation 133 (hereinafter referred to as an "end threshold value"). The arithmetic unit 120 performs a computing process to calculate the end threshold value Sth on the basis of the detection signal DS output from the detection unit during a period of time during which irradiation is applied to the pixel array 101 having the switch elements T of the pixels P that are set in a non-conducting state by the drive circuit 102. In this manner, the end threshold value that takes into account a delay of the radiation 133 (e.g., a wave tail) can be set. By controlling the start of an operation to transfer an electric signal based on the accumulated electric carriers from the pixel P using the end threshold value Sth calculated in this manner, a negative effect on the image signal can be eliminated.

In addition, the radiation image pickup system includes a control console 140, a control computer 150, and a display unit 160. The control console 140 is used to input information regarding a subject and an image capturing condition including an irradiation condition. The control console 140 transmits the information and the image capturing condition to the control computer 150. The control computer 150 sets the information and the image capturing condition in the radiation image pickup apparatus 100. The display unit 160 displays an image based on the digital image signal subjected to the image processing in the control computer 150 that has received a digital image signal from the radiation image pickup apparatus 100.

The radiation image pickup apparatus 100 further includes a signal processing unit 106 having a readout circuit 103, an A/D converter 104, and a digital signal processing unit 105, a power supply unit 107, a control unit 108. The radiation image pickup apparatus 100 still further includes a detection unit formed from at least one of the detection circuit 110 and a detection element 110' and the arithmetic unit 120.

According to the present exemplary embodiment, in each of the pixels P, one of the two electrodes of the conversion element S (a first electrode) is electrically connected to one of the two main terminals of the switch element T. The other electrode (a second electrode) is electrically connected to, via a bias line Vs, a bias power supply VS that is included in a power supply unit 107 and that supplies a bias voltage. The control terminal of the switch element T is connected to a drive line G. A drive signal including a conducting voltage and a non-conducting voltage is supplied from the drive circuit 102 to the control terminal of the switch element T via the drive line G. The drive line G is selectively connected to a conducting power supply VON for supplying the conducting voltage via a conducting voltage line Von and the drive circuit 102 and a non-conducting power supply VOFF for supplying the non-conducting voltage via a non-conducting voltage line Voff and the drive circuit 102. Note that the conducting power supply VON and the non-conducting power supply VOFF are included in the power supply unit 107. The control terminals of all of the plurality of switch elements (e.g., switch elements T11 to T14) arranged in the row direction are electrically connected to a drive line G1 in the first row. Accordingly, a drive signal is provided from the drive circuit 102 to all of the switch elements arranged in one of the rows via the drive line G on a row-by-row basis. According to the present exemplary embodiment, one of the main terminals of the switch element T is electrically connected to the first electrode of the conversion element S, and the other main terminal is connected to a signal line Sig extending in the column direction. The signal line Sig is connected to a reference power supply VREF that is included in the power supply unit 107 and that supplies a reference voltage via a reference voltage line Vref. The other main terminal of each of the plurality of switch elements arranged in the column direction (e.g., switch elements T11 to T41) is electrically connected to a signal line Sig1 in the first column. Accordingly, when a conducting voltage is supplied to the control terminal of a switch element in some row and, thus, the switch element is in a conducting state, an electric signal in accordance with the electric carriers in the conversion element is transferred to a readout circuit 103 via the signal line. The signal line Sig1 and signal lines Sig2 to Sig4 that are arranged transfer electric signals output from a plurality of pixels in the same row to the readout circuit 103 in parallel. In addition, the pixel array 101 includes a capacitive line Vd that allows capacitive coupling with the drive line G via a capacitance Cd. In addition, the power supply unit 107 includes a capacitance power supply VD for supplying a constant voltage to the capacitive line Vd.

The readout circuit 103 includes an amplifying circuit unit 103a, a sampling and holding circuit unit 103b, a multiplexer 103c, and an output buffer circuit 103d. The amplifying circuit unit 103a amplifies the electric signals output from the pixel array 101 in parallel. The amplifying circuit unit 103a includes the amplifying circuit for each of the signal lines. The amplifying circuit includes an operational amplifier A that amplifies the readout electric signal and output the electric signal, an integral capacitance Cf, and a reset switch RC that resets integral capacitance. The output signal is input to an inverting input terminal of the operational amplifier A, and the amplified electric signal is output from an output terminal of the operational amplifier A. At that time, a reference power supply VREF is connected to a non-inverting input terminal of the operational amplifier A via a reference power supply line Vref. The sampling and holding circuit unit 103b samples and holds the electric signal output from the amplifying circuit unit 103a. The sampling and holding circuit unit 103b includes a sample-and-hold circuit for each of the amplifying circuits. The sample-and-hold circuit includes a sampling switch SH and a sampling capacitor Ch. The multiplexer 103c and the output buffer circuit 103d sequentially output the electric signals read from the sampling and holding circuit unit 103b in parallel in the form of an image signal formed from serial signals. The multiplexer 103c includes a switch SW provided for each of the sample-and-hold circuits. By sequentially selecting the switches SW, an operation for converting parallel signals to serial signals can be performed. Through such a configuration, the readout circuit 103 reads an image signal based on the electric signal output from the pixel array 101 that is driven.

An A/D converter 104 converts an analog signal converted into serial signals into a digital signal and transfers the digital signal to a digital signal processing unit 105. The digital signal processing unit 105 performs simple digital signal processing, such as a digital multiplexing process and an offset correction process, on the digital signal output from the A/D converter 104 and outputs a digital image signal.

The detection unit includes at least one of the detection circuit 110 and the detection element 110'. The detection circuit 110 outputs a detection signal DS. The detection signal DS is an electric current flowing in at least one of a bias line Vs, the reference voltage line Vref, the conducting voltage line Von, the non-conducting voltage line Voff, and the capacitive line Vd. Alternatively, the detection signal DS is a signal based on the electric current. Note that an electric current flowing through the drive line G is equivalent to an electric current flowing through one of the conducting voltage line Von and the non-conducting voltage line Voff. In addition, an electric current flowing through the reference voltage line Vref is equivalent to an electric current flowing through the signal line Sig which is capacitively coupled with the drive line G. That is, the detection circuit 110 can detect an electric current that flows through any one of the drive line G, the bias line Vs, the signal line Sig which is a coupled line capacitively coupled with the drive line, and the capacitive line Vd disposed in the pixel array 101. An electric current that flows through any one of these lines varies with a variation of the potential based on the electric carriers generated in the conversion element S when the conversion element S is irradiated. That is, the electric current that flows through any one of these lines reflects the electric carriers generated in the conversion element S due to the irradiation. Accordingly, by detecting such an electric current, the presence/absence of irradiation of the pixel array 101 and the intensity of the irradiation can be detected. For example, the detection circuit 110 has a configuration in which the current/voltage conversion circuit that converts an electric current into a voltage is disposed for each of a variety of types of lines, the output of one of the current/voltage conversion circuit is selected, the band is limited, and analog-to-digital conversion is performed. Alternatively, the detection circuit 110 may output the detection signal DS on the basis of a signal output from a signal processing unit 106. The detection circuit 110 is disposed separately from the pixel array 101 at a position at which irradiation can be applied. For example, the detection circuit 110 may be disposed on the opposite side of the pixel array 101 from the radiation generating apparatus 130. In addition, the detection circuit 110 includes an indirect type conversion element or a direct type conversion element and, thus, outputs the detection signal DS which is one of an electric signal converted from radiation or light converted by a wavelength conversion element and a signal based on the electric signal.

The arithmetic unit 120 outputs, to a control unit 108, a control signal RS that controls start and end of irradiation (hereinafter referred to as a "radiation signal") on the basis of the computed end threshold value Sth. The arithmetic unit 120 includes a selecting unit 121, a temporary storage unit 122, a calculator 123, a storage unit 124, and a comparator 125. Upon receiving a mode selection signal generated by the control unit 108 when the control unit 108 receives a control signal from a control computer 150, the selecting unit 121 selects one of the temporary storage unit 122 and the comparator 125. Thereafter, the selecting unit 121 outputs the input detection signal DS to the selected one of the temporary storage unit 122 and the comparator 125. The temporary storage unit 122 stores the detection signal DS that is varying and outputs the detection signal DS to the calculator 123. The calculator 123 calculates the end threshold value Sth on the basis of the detection signal DS stored in the temporary storage unit 122 and outputs the calculated end threshold value Sth to the storage unit 124. The storage unit 124 stores the calculated end threshold value Sth in association with each of irradiation conditions (described in more detail below) acquired from the control computer 150 via the control unit 108. The comparator 125 selects, from among the end threshold values each stored in the storage unit 124 so as to correspond to one of the irradiation conditions, an end threshold value corresponding to the irradiation condition acquired from the control computer 150 via the control unit 108. Thereafter, the comparator 125 compares the selected end threshold value Sth with the input detection signal DS and generates a radiation signal RS. The comparator 125 outputs the generated radiation signal RS to the control unit 108. Note that the arithmetic unit 120 can perform a computation process to further compute a threshold value Sth' used to detect start of the irradiation (hereinafter referred to as a "start threshold value") on the basis of the detection signal DS. In such a case, the calculator 123 can further calculate the start threshold value Sth' on the basis of the variation of the detection signal DS and output the calculated start threshold value Sth' to the storage unit 124. In addition, the storage unit 124 can store the calculated start threshold value Sth' in association with the irradiation condition. The comparator 125 can further compare the start threshold value Sth' selected in accordance with the irradiation condition with the input detection signal DS, generate a radiation signal RS, and output the radiation signal RS. Note that the operation performed by the arithmetic unit 120 is described in more detail below.

The control unit 108 supplies a variety of control signals to the drive circuit 102, the signal processing unit 106, the power supply unit 107, and the detection unit in accordance with the control signal output from the control computer 150 and the radiation signal RS output from the arithmetic unit 120 and controls the operation performed by the radiation image pickup apparatus 100. In addition, the control unit 108 transmits the irradiation condition acquired from the control computer 150 to the storage unit 124. In addition, the control unit 108 transmits a mode selection signal acquired from the control computer 150 to the selecting unit 121. Note that the operation performed by the control unit 108 is described in more detail below.

Figure 2:
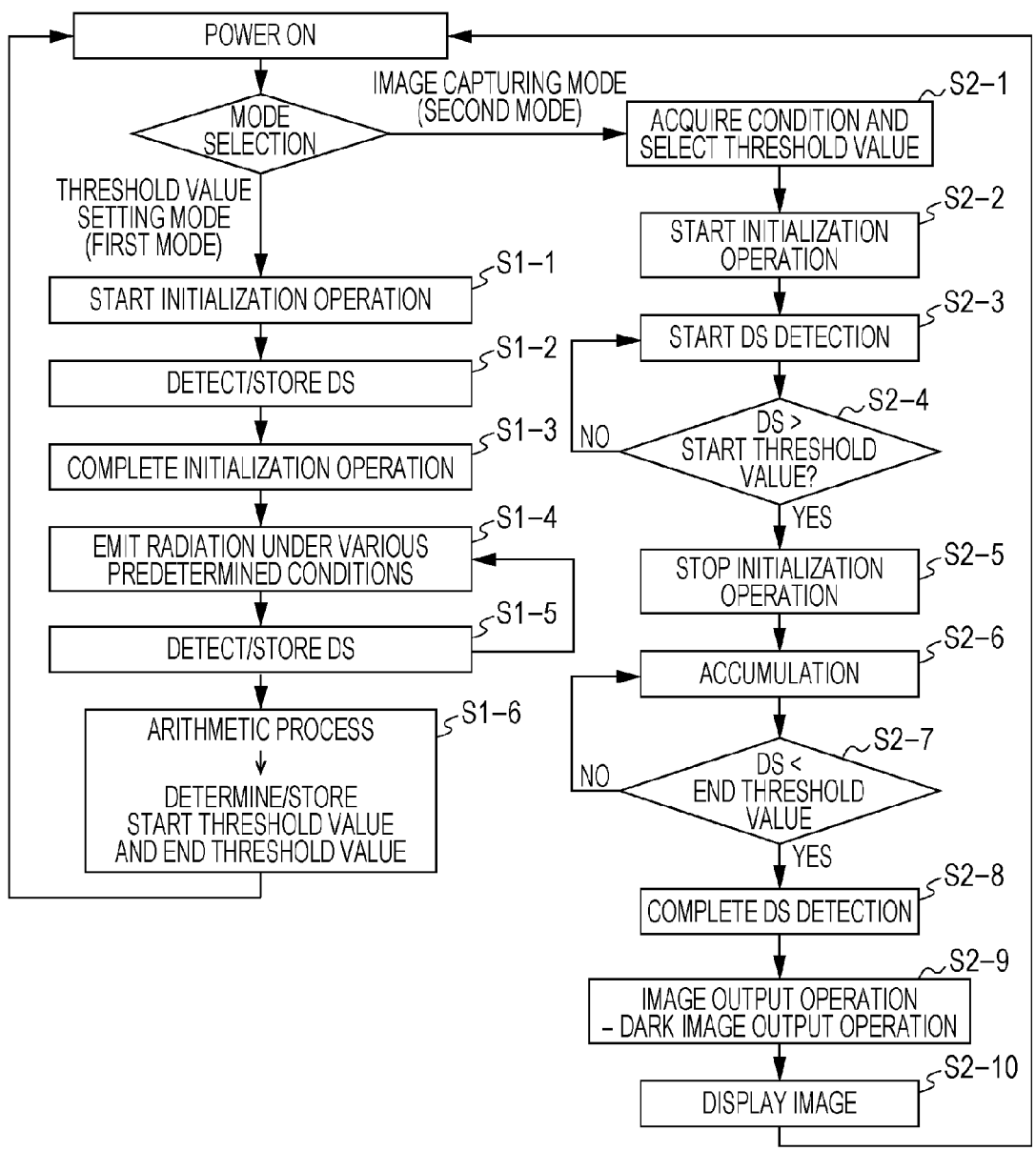
FIG. 2 is a flowchart illustrating the operations performed by the radiation image pickup apparatus and the radiation image pickup system according to a first exemplary embodiment.
Figure 3A:
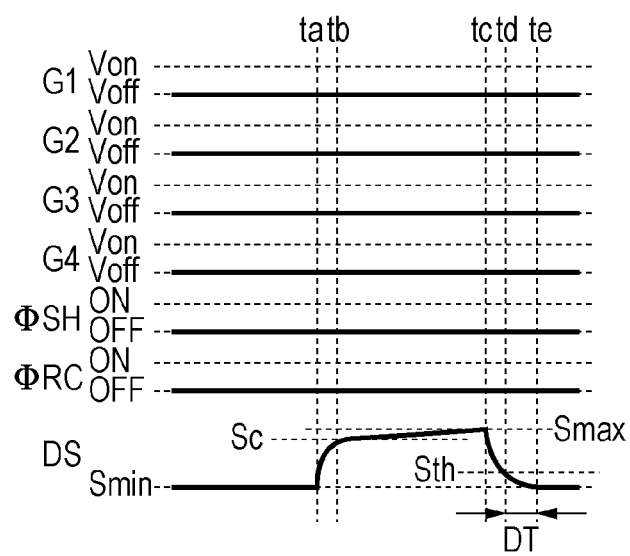
FIG. 3A is a timing diagram illustrating an exemplary operation for calculating a threshold value used for detecting end of irradiation according to the first exemplary embodiment.
Figure 3C:
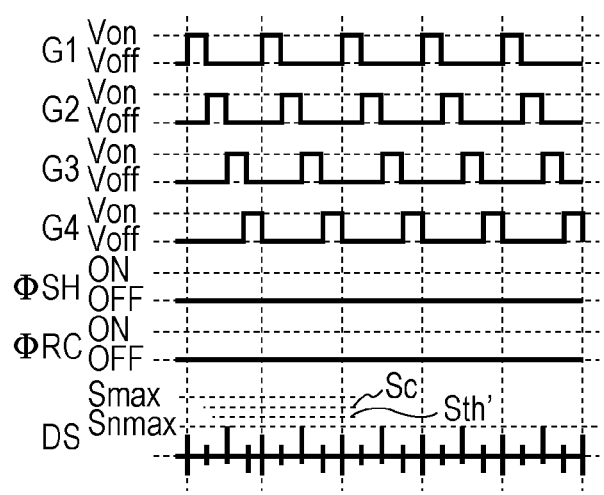
FIG. 3C is a timing diagram illustrating an exemplary operation for calculating a threshold value used for detecting the start of irradiation.

The detection of irradiation and exemplary operations and control performed in relation to the detection according to the present exemplary embodiment are described next with reference to FIG. 2, FIGS. 3A to 3C, and FIG. 4. FIG. 2 is a flowchart illustrating the operations performed by the radiation image pickup apparatus and the radiation image pickup system according to a first exemplary embodiment. FIG. 3A is a timing diagram illustrating the operation to calculate the end threshold value Sth. FIG. 3B illustrates a table stored in a storage unit and defining a correspondence between a condition and a threshold value. FIG. 3C is a timing diagram illustrating the operation to calculate the start threshold value Sth'.

As illustrated in FIG. 2, when the radiation image pickup apparatus 100 is powered on, the control unit 108 selects one of a threshold value setting mode (a first mode) and an image capturing mode (a second mode) on the basis of the mode selection signal received from the control computer 150.

If the mode selection signal indicating that the first mode is to be selected is supplied to the control unit 108, the control unit 108 instructs the selecting unit 121 to connect to the temporary storage unit 122 so that the detection signal DS is output to the temporary storage unit 122. In addition, the control unit 108 supplies a variety of control signals to the signal processing unit 106, the power supply unit 107, and the detection unit so that these units operate in the first mode. The power supply unit 107 supplies a bias voltage to the pixel array 101, supplies the conducting voltage and the non-conducting voltage to the drive circuit 102, and supplies the reference voltage to the readout circuit 103 via the detection circuit 110.

Subsequently, in step S1-1 illustrated in FIG. 2, the control unit 108 supplies a control signal to the drive circuit 102. Upon receiving the control signal, the drive circuit 102 outputs a drive signal so that a conducting voltage is sequentially output to drive lines G1 to G8. In this manner, as illustrated in FIG. 3C, an initialization operation K in which all of the switch elements T are sequentially set in a conducting state on a row-by-row basis is started.

Subsequently, during a period of time indicated in step S1-2 illustrated in FIG. 2, the pixel array 101 being subjected to the initialization operation K has at least one of the switch elements T of the plurality of pixels P that is set in the conducting state by the drive circuit 102. In addition, the radiation 133 is not emitted from the radiation generating apparatus 130 to the pixel array 101. During such a period, the detection signal DS output from the detection unit includes noise that is synchronized with the operation performed by the switch element T (hereinafter referred to as a "switching noise"). Thus, the detection signal DS varies, as illustrated in FIG. 3C. The detection signal DS that varies in this manner is output to the temporary storage unit 122 via the selecting unit 121 and is stored in the temporary storage unit 122. The calculator 123 calculates the highest value Snmax of the switching noise, which is the highest value of the detection signal DS output during the period of time, on the basis of the detection signal DS stored in the temporary storage unit 122. Thereafter, the calculator 123 stores the obtained highest value Snmax of the switching noise in the storage unit 124.

Subsequently, in step S1-3 illustrated in FIG. 2, the control unit 108 supplies a control signal to the drive circuit 102. After supplying a conducting voltage to the drive line G4, the drive circuit 102 continuously supplies a non-conducting voltage to all of the drive lines. Thereafter, the initialization operation K is completed.

Subsequently, during a period of time indicated in step S1-4 illustrated in FIG. 2, the drive circuit 102 still continuously supplies a non-conducting voltage to all of the drive lines. Thus, as illustrated in FIG. 3A, the switch elements T of the pixels P in the pixel array 101 are set in a non-conducting state by the drive circuit 102. Thereafter, emission of the radiation 133 from the radiation generating apparatus 130 under a predetermined irradiation condition set by the radiation control apparatus 131 is started and completed. The detection signal DS output from the detection unit during such a period of time varies with the intensity of the emitted radiation 133, as schematically illustrated in FIG. 3A. For example, as illustrated in FIG. 3A, a variation curve has the lowest value 5 min when irradiation is not applied. The variation curve starts rising at the time ta, has a signal value of Sc at a time tb as an inflection point, and has the highest value Smax at the time tc. After the time tc, the variation curve gradually falls from the highest value Smax with a delay and has the lowest value 5 min at a time te. The detection signal DS having such a variation is output to the temporary storage unit 122 via the selecting unit 121 and is stored in the temporary storage unit 122. Subsequently, in step S1-5 illustrated in FIG. 2, the calculator 123 calculates the lowest value 5 min, the highest value Smax, and the inflection point Sc on the basis of the detection signal DS stored in the temporary storage unit 122. Thereafter, the calculator 123 stores the obtained information in the storage unit 124. In addition, the calculator 123 may calculate the times ta, tb, tc, and te and store the calculated times in the storage unit 124. For example, the times are measured by a timing measuring unit (not illustrated) separately provided. Subsequently, the calculator 123 extracts the lowest value 5 min and the highest value Smax from plots of the stored detection signal DS. Thereafter, an approximation expression is generated from the plots of the detection signal DS in a region from the time to to the time tc at which the highest value Smax appears, and the inflection point Sc is computed using the approximation expression. At that time, the storage unit 124 acquires the irradiation condition from the control computer 150 via the control unit 108 and stores the values in association with the irradiation condition. Step S1-4 and S1-5 are performed for each of the irradiation conditions.

Subsequently, in step S1-6 illustrated in FIG. 2, the calculator 123 calculates the end threshold value Sth on the basis of a variety of values stored in the storage unit 124. In addition, the calculator 123 calculates the start threshold value Sth' on the basis of a variety of values stored in the storage unit 124. The start threshold value Sth' is set so as to be in the range between the highest value Smax and the highest value Snmax of the switching noise and, preferably, between the inflection point Sc and the highest value Snmax of the switching noise. This is because as the start threshold value Sth' decreases, a period of time required from the start of irradiation to detection of the start of irradiation decreases. Thus, the detection accuracy can be increased. By employing such setting, start of irradiation can be detected in a short time without being influenced by switching noise. In contrast, the end threshold value Sth is set so as to be in the range between the highest value Smax and the lowest value 5 min and, preferably, between the start threshold value Sth' and the lowest value 5 min. Since at the end of irradiation, the switch element T is set in a non-conducting state, switching noise need not be taken into account. Accordingly, the end threshold value Sth can be set so as to be lower than the start threshold value Sth'. Accordingly, the end of irradiation can be detected without being influenced by the wave tail. In addition, the calculator 123 calculates a time interval DT between a time td at which the value of the detection signal DS is lower than the end threshold value Sth and the time to at which the value of the detection signal DS is the lowest value 5 min and stores the calculated time interval DT in the storage unit 124. When starting an image output operation in the radiation image capturing operation (described in more detail below), the control unit 108 may use the stored time interval DT as a predetermined time interval from the time the detection signal DS is lower than the end threshold value Sth to the time electrical continuity of the switch element T starts. Such processing is performed by the calculator 123 and the storage unit 124 for each of the irradiation conditions. The end threshold value Sth obtained for each of the irradiation conditions is stored in the storage unit 124 in association with the irradiation condition by the calculator 123. Thus, a plurality of the end threshold values each corresponding to one of the irradiation conditions are stored in the storage unit 124. In the example illustrated in FIG. 3B, 108 end threshold values Sth1 to Sth108 each corresponding to one of 108 irradiation conditions are stored in the storage unit 124 in the form of a lookup table. After the threshold values corresponding to all of the irradiation conditions are calculated and stored, the processing for the first mode is completed. Note that step S1-6 corresponds to a first step of the present invention.

Figure 4:
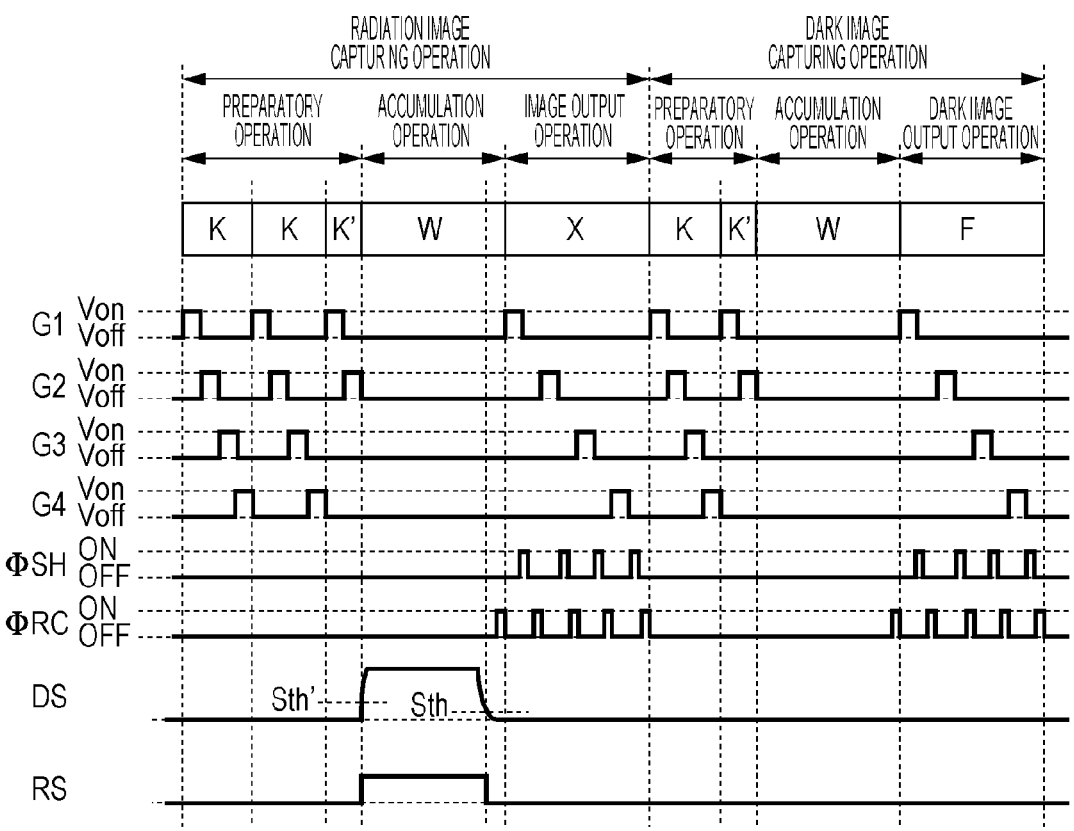
FIG. 4 is a timing diagram illustrating the operation performed by the radiation image pickup apparatus.

The second mode is described next. As illustrated in FIG. 4, an exemplary operation performed by the radiation image pickup apparatus according to the present exemplary embodiment includes a radiation image capturing operation and a dark image capturing operation. Note that the dark image capturing operation is not essential in the present exemplary embodiment. However, it is desirable to perform the dark image capturing operation in order to increase the accuracy of offset correction.

Upon receiving the mode selection signal indicating that the second mode is selected, the control unit 108 provides a mode selection signal indicating selection of the second mode (i.e., the image capturing mode) to the selecting unit 121. Upon receiving the control signal, the selecting unit 121 selects connection to the comparator 125 so as to output the detection signal DS to the comparator 125. Subsequently, in step S2-1 illustrated in FIG. 2, the control unit 108 selects the start threshold value Sth' and the end threshold value Sth corresponding to the irradiation condition acquired from the control computer 150 and stored in the storage unit 124 and supplies the selected start threshold value Sth' and the end threshold value Sth to the comparator 125.

Subsequently, in step S2-2 illustrated in FIG. 2, the control unit 108 supplies a control signal to the drive circuit 102. Upon receiving the control signal, the drive circuit 102 outputs a drive signal so that a conducting voltage is sequentially supplied to the drive lines G1 to G4. In this manner, the initialization operation K in which all of the switch elements T are sequentially set in the conducting state on a row-by-row basis is started. As illustrated in FIG. 4, the initialization operation K is performed until start of irradiation is detected.

Subsequently, in step S2-3 illustrated in FIG. 2, the detection unit starts detecting the detection signal DS during a preparatory operation including the initialization operation K and outputs the detection signal DS to the comparator 125 via the selecting unit 121. Subsequently, in step S2-4 illustrated in FIG. 2, the comparator 125 compares the value of the detection signal DS with the start threshold value Sth' and generates the radiation signal RS. Thereafter, the comparator 125 outputs the radiation signal RS to the control unit 108. In this case, as illustrated in FIG. 4, the radiation signal RS has a value of Lo if the value of the detection signal DS does not exceed the start threshold value Sth'. In contrast, the radiation signal RS has a value of Hi if the value of the detection signal DS exceeds the start threshold value Sth' and, thus, irradiation is started. If the value of the detection signal DS does not exceed the start threshold value Sth', the processing returns to step S2-3 illustrated in FIG. 2. Thereafter, steps S2-3 and S2-4 illustrated in FIG. 2 are repeatedly performed until the value of the detection signal DS exceeds the start threshold value Sth'. If the value of the detection signal DS exceeds the start threshold value Sth', the radiation signal RS is set to Hi, which is supplied to the control unit 108. The control unit 108 supplies a control signal to the drive circuit 102. Thus, the drive circuit 102 stops supplying the conducting voltage to the drive line G. As illustrated in FIG. 4, in an initialization operation K', start of irradiation is detected during a period of time in which the drive circuit 102 supplies the conducting voltage to the drive line G2. Thus, the drive circuit 102 does not supply the conducting voltage to the drive lines G3 and G4. All of the switch elements T remain in the non-conducting state. In this manner, in step S2-5 illustrated in FIG. 2, the operation of the pixel array 101 is controlled in response to start of irradiation so that the initialization operation K' is completed before all of the pixel rows are processed. Thus, the operation performed by the radiation image pickup apparatus 100 proceeds from the preparatory operation to an accumulation operation W.

Subsequently, in step S2-6 illustrated in FIG. 2, the pixel array 101 that performs an accumulation operation is irradiated and, thus, electric carriers in accordance with the radiation is accumulated in each of the pixels P. Thereafter, in step S2-7 illustrated in FIG. 2, the comparator 125 compares the value of the detection signal DS with the end threshold value Sth and generates the radiation signal RS. Thereafter, the comparator 125 outputs the radiation signal RS to the control unit 108. At that time, as illustrated in FIG. 4, if the value of the detection signal DS is not lower than the end threshold value Sth, the radiation signal RS has a value of Hi. However, if the value of the detection signal DS is lower than the end threshold value Sth, the value of the radiation signal RS is changed from Hi to Lo and, thus, irradiation is completed. If the value of the detection signal DS is not lower than the end threshold value Sth, the processing returns to step S2-6 illustrated in FIG. 2. Thereafter, steps S2-6 and S2-7 illustrated in FIG. 2 are repeatedly performed until the value of the detection signal DS becomes lower than the end threshold value Sth. If the value of the detection signal DS becomes lower than the end threshold value Sth, the radiation signal RS is set to Lo and is supplied to the control unit 108. Note that step S2-6 corresponds to a second step of the present invention.

Subsequently, in step S2-8 illustrated in FIG. 2, upon receiving the radiation signal RS having a value of Lo, the control unit 108 supplies a control signal to the detection unit. Thus, the detection unit stops outputting the detection signal DS. In step S2-9 illustrated in FIG. 2, the control unit 108 supplies control signals to the drive circuit 102, the signal processing unit 106, and the power supply unit 107. The power supply unit 107 supplies the reference voltage to the signal processing unit 106. As illustrated in FIG. 4, the drive circuit 102 outputs a drive signal so that a conducting voltage is sequentially supplied to the drive lines G1 to G4. Thus, all of the switch elements T are sequentially set in the conducting state on a row-by-row basis. Accordingly, the radiation image pickup apparatus 100 performs an image output operation X for outputting an electric signal in accordance with the irradiation from the pixel array 101 to the readout circuit 103. In such a case, it is desirable that the control unit 108 control the drive circuit 102 so that a conducting voltage is supplied to the drive line G1 which is the drive line to which the conducting voltage is supplied first after the predetermined time interval DT stored in the storage unit 124 has elapsed since reception of the radiation signal RS of Lo. That is, it is desirable that the control unit 108 control the drive circuit 102 so that step S2-9 starts after the predetermined time interval DT has elapsed since completion of step S2-7. This is because irradiation of the switch element T caused by a wave tail in step S2-9 is reduced and, thus, a negative effect on the image signal can be eliminated. In the above-described manner, the radiation image pickup apparatus 100 performs the preparatory operation, the accumulation operation W, and the image output operation X. At that time, it is desirable that the operating period of the initialization operation K be shorter than that of the image output operation X. Note that according to the present exemplary embodiment, the operating period of the initialization operation K is shorter than that of the image output operation X. Accordingly, in the image output operation X, the conducting voltage is supplied to the drive line G1 instead of the drive line G3 to which the conducting voltage is not supplied in the initialization operation K. This is because since the operating period of the initialization operation K is short, the accumulation time is much shorter as compared with the case in which the conducting voltage is initially supplied to the drive line G3. In addition, if the conducting voltage is initially supplied to the drive line G3, the difference in accumulation time between the pixel P connected to the drive line G3 and the pixel P connected to the drive line G2 becomes large and, thus, an impact on an obtained image signal becomes large as compared with the case in which the conducting voltage is initially supplied to the drive line G1. Subsequently, the radiation image pickup apparatus 100 performs a dark image capturing operation. Like the radiation image capturing operation, the dark image capturing operation includes a preparatory operation including at least one initialization operation K and the initialization operation K', the accumulation operation W, and a dark image output operation F. Note that in the accumulation operation W included in the dark image capturing operation, radiation is not emitted. In addition, the dark image output operation F is performed to output an electric signal based on dark output caused by a dark current generated in the conversion element S from the pixel array 101 to the readout circuit 103. The operation performed by the radiation image pickup apparatus 100 is the same as the image output operation X. Note that step S2-9 corresponds to a third step of the present invention.

Subsequently, in step S2-10 illustrated in FIG. 2, the digital signal processing unit 105 performs offset correction on the basis of a digital signal obtained in the image output operation X and the dark image capturing operation F and converted by the A/D converter 104. Thereafter, the digital signal processing unit 105 outputs a digital image signal to the control computer 150. The control computer 150 performs image processing on the received digital image signal and outputs the digital image signal to the display unit 160. The display unit 160 displays an image based on the digital image signal subjected to the image processing.

Figure 5:
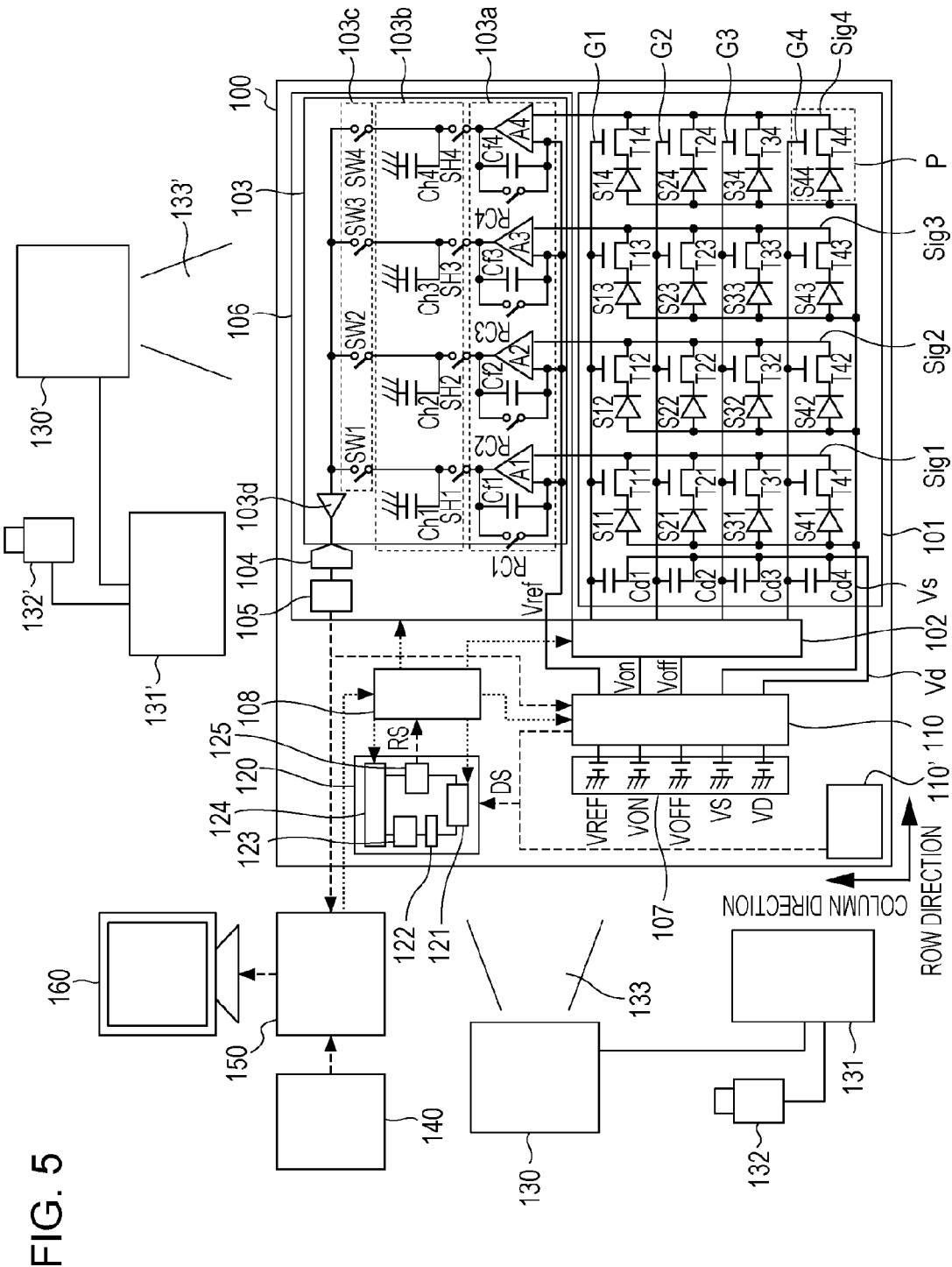
FIG. 5 is a schematic equivalent circuit diagram illustrating another radiation image pickup system.

Note that in FIG. 1A, the radiation image pickup system including one radiation generating machine formed from the radiation generating apparatus 130, the radiation control apparatus 131, and the exposure button 132 is illustrated. However, the present invention is not limited thereto. For example, as illustrated in FIG. 5, the present invention is applicable to a radiation image pickup system including a plurality of radiation generating apparatuses. In such a case, since a delay of irradiation (e.g., a wave tail) is specific to each of the radiation generating apparatuses, it is desirable that as illustrated in FIG. 3B, a lookup table corresponding to each of the radiation generating apparatuses be prepared.

While the present exemplary embodiment has been described with reference to a processing flow in which both the start threshold value and the end threshold value are calculated in the first mode, the processing flow according to the present invention is not limited thereto. For example, the start threshold value and the end threshold value may be calculated in different modes.

Second Exemplary Embodiment

Figure 6A:
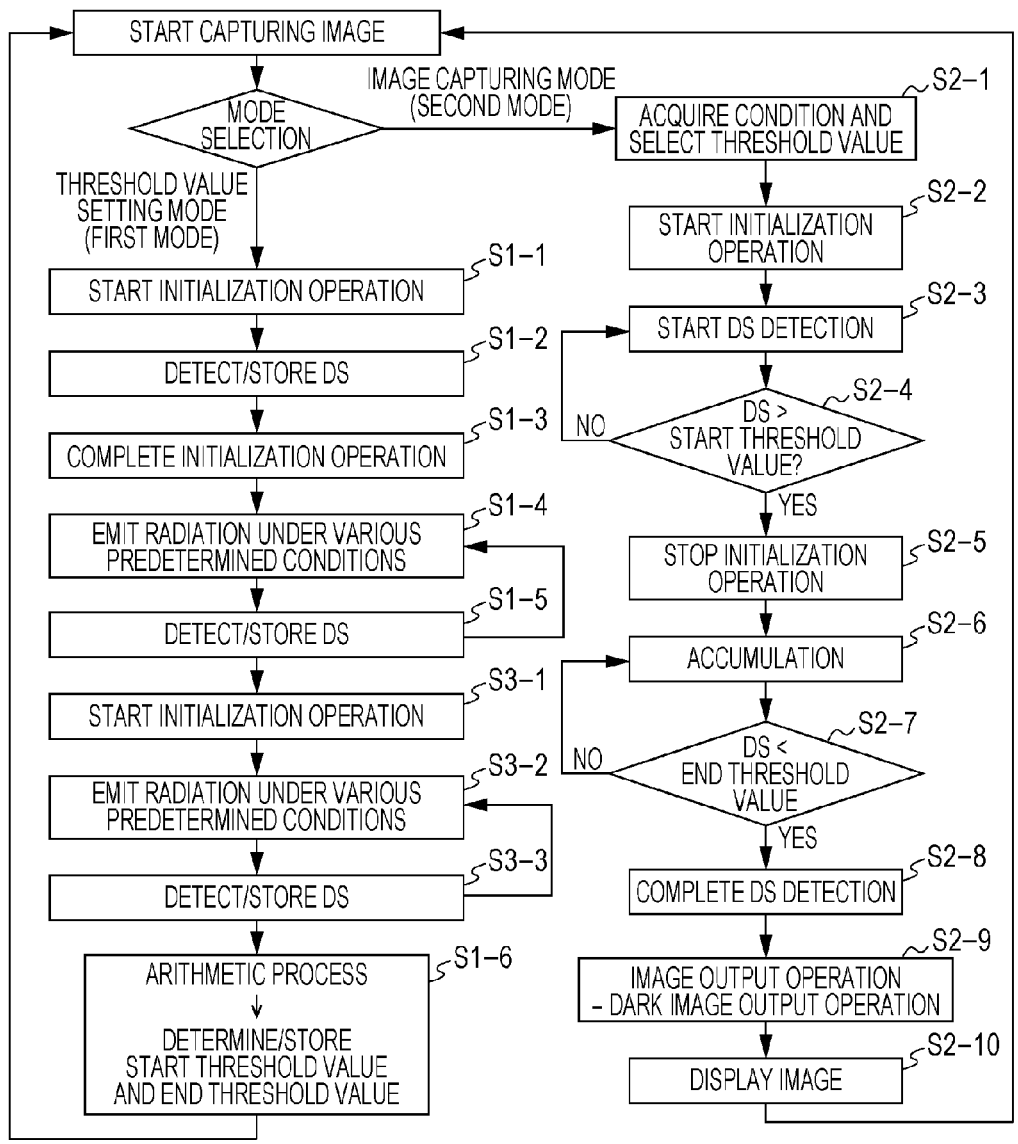
FIG. 6A is a flowchart illustrating exemplary operations performed by a radiation image pickup apparatus and a radiation image pickup system according to a second exemplary embodiment.
Figure 6B:
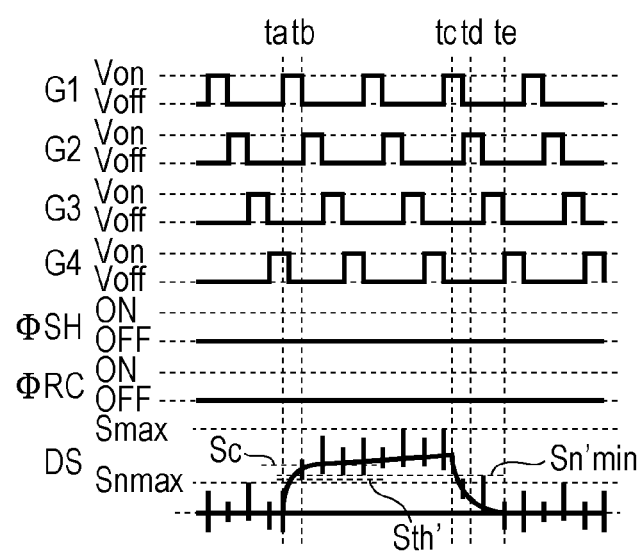
FIG. 6B is a timing diagram illustrating the operation for calculating a threshold value used for detecting start of irradiation.

Detection of exposure to radiation and an exemplary operation and control related to the detection according to a second exemplary embodiment are described next. FIG. 6A is a flowchart illustrating exemplary operations performed by a radiation image pickup apparatus and a radiation image pickup system according to the second exemplary embodiment. FIG. 6B is a timing diagram illustrating a different operation for calculating the start threshold value Sth'. Note that the same numbering is used in referring to a configuration and a step in FIGS. 6A and 6B as are used above in describing the first exemplary embodiment, and detailed descriptions of the configuration and the step are not repeated.

According to the present exemplary embodiment, as illustrated in FIG. 6A, a flowchart of the first mode can be obtained by adding steps S3-1 to S3-3 (described in more detail below) between steps S1-5 and S1-6 of the flowchart illustrated in FIG. 2, which is a flowchart for the first mode of the first exemplary embodiment.

In step S3-1 that follows step S1-5 illustrated in FIG. 6A, the control unit 108 supplies a control signal to the drive circuit 102. The drive circuit 102 outputs a drive signal so that a non-conducting voltage is sequentially supplied to the drive lines G1 to G8. In this manner, as illustrated in FIG. 6B, the initialization operation K in which all of the switch elements T are sequentially set in a conducting state on a row-by-row basis is started.

Subsequently, during a period of time indicated by step S3-2 illustrated in FIG. 6A, in the pixel array 101 being subjected to the initialization operation K, the switch elements T of the plurality of pixels P are sequentially set in the conducting state by the drive circuit 102. In addition, emission of the radiation 133 from the radiation generating apparatus 130 under a predetermined irradiation condition set by the radiation control apparatus 131 is started and completed. The detection signal DS output from the detection unit during such a period of time varies with the intensity of the emitted radiation 133, as illustrated in FIG. 6B. In step S3-3 illustrated in FIG. 6A, the detection signal DS having such a variation is output to the temporary storage unit 122 via the selecting unit 121 and is stored in the temporary storage unit 122. Subsequently, the calculator 123 applies the time tb indicating the inflection point Sc obtained in step S1-4 illustrated in FIG. 2 and the time tc indicating the highest value Smax to the variation illustrated in FIG. 6B on the basis of the detection signal DS stored in the temporary storage unit 122. Thereafter, the calculator 123 calculates the lowest value Sn'min of the switching noise, which is the lowest value of the detection signal DS during an irradiation period between the time tb and the time tc and stores the lowest value Sn'min in the storage unit 124. At that time, the storage unit 124 acquires the irradiation condition from the control computer 150 via the control unit 108 and stores the values in association with the irradiation condition. Steps S3-2 and S3-3 are performed for each of the irradiation conditions.

Subsequently, in step S1-6 illustrated in FIG. 6A. The calculator 123 calculates the start threshold value Sth' using the lowest value Sn'min of the switching noise in addition to calculating the values used in step S1-6 illustrated in FIG. 2. In some cases, the lowest value Sn'min of the switching noise during the irradiation period is higher than the highest value Snmax of the switching noise and lower than the highest value Smax. In such a case, the start threshold value Sth' is set so as to be in the range between the lowest value Sn'min of the switching noise during the irradiation period and the highest value Sn'max of the switching noise. By employing such setting, start of irradiation can be detected without being influenced by switching noise in a shorter time than in the first exemplary embodiment.

Figure 7:
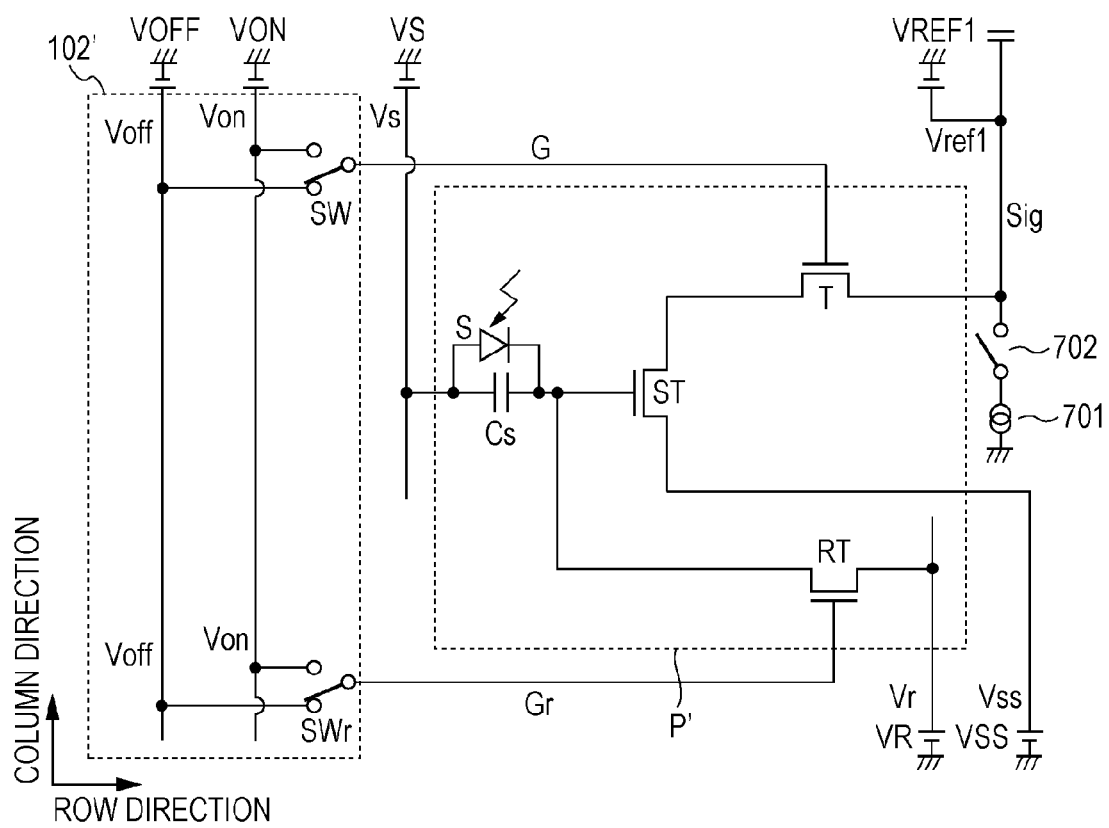
FIG. 7 is a schematic equivalent circuit diagram illustrating the configuration of a pixel of a different radiation image pickup apparatus.

While the radiation image pickup apparatuses illustrated in FIGS. 1A and 5 have been described with reference to the conversion element S and the switch element T in each of the pixels P (i.e., a so-called passive pixel), the configuration of the present invention is not limited thereto. For example, as illustrated in FIG. 7, the radiation image pickup apparatus may use a so-called active pixel which further includes an amplifying element ST and a reset element RT. At that time, a transistor including a control terminal (a gate electrode) and two main terminals is used as the amplifying element ST. The control terminal of the transistor is connected to one of electrodes of the conversion element S. One of the main terminals of the transistor is connected to the switch element T, and the other main terminal is connected to an operating power supply VSSs that supplies an operating voltage via an operating power supply line Vss. In addition, a constant current source 701 is connected to the signal line Sig via a switch 702. Thus, a source follower circuit is formed together with the amplifying element ST. Furthermore, a transistor including a control terminal (a gate electrode) and two main terminals is used as the reset element RT. One of the main terminals is connected to a reset power supply VR that supplies a reset voltage via a reset line Vr. The other main terminal is connected to the control electrode of the amplifying element ST. Like the drive line G, a control electrode of the reset element RT is connected to the drive circuit 102 via a reset drive line Gr. It is desirable that the detection circuit 110 be capable of outputting the detection signal DS on the basis of an electric current flowing in one of the reset power supply VR and the operating power supply line Vss in addition to the above-described lines. Furthermore, the power supply unit 107 further includes the reset power supply VR and the operating power supply VSS. Still furthermore, the reset line Vr and the operating power supply line Vss are included in the above-described coupled line.

Note that the exemplary embodiments of the present invention can be realized by, for example, a computer included in the control unit 108 or the control computer 150 executing a program. In addition, a computer-readable recording medium used for supplying the program to the computer (e.g., a compact disc read only memory (CD-ROM) that stores the program) and a transfer medium that transfers the program (e.g., the Internet) can be used as an exemplary embodiment of the present invention. Furthermore, the program can be used as an exemplary embodiment of the present invention. The program, the recording medium, the transfer medium, and a program product are encompassed by the invention. Still furthermore, a combination that is easily conceivable from the first or second exemplary embodiment is encompassed by the invention.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Application No. 2012-152393 filed Jul. 6, 2012, which is hereby incorporated by reference herein in its entirety.

What is claimed is:

1. A method for controlling a radiation image pickup apparatus, the radiation image pickup apparatus including a pixel array having a plurality of pixels arranged in a matrix, a drive circuit, and a detection unit, each of the pixels including a conversion element and a switch element and converting radiation into an electric signal, the drive circuit controlling the switch element between a conducting state and a non-conducting state, the detection unit outputting a signal varying with an intensity of irradiation of the pixel array, the method comprising:

switching the radiation image pickup apparatus between a first mode and a second mode, wherein in the first mode, an end threshold value used for detecting end of irradiation of the pixel array is calculated on the basis of the signal output from the detection unit during a period of time during which irradiation is applied to the pixel array in which the switch elements of the plurality of pixels are set in the non-conducting state by the drive circuit, and wherein in the second mode, the switch elements of the plurality of pixels are sequentially set in the conducting state by the drive circuit on a row-by-row basis if a value of the signal output from the detection unit is lower than the end threshold value during a period of time during which irradiation is applied to the pixel array in which the switch elements of the pixels are set in the non-conducting state by the drive circuit after the first mode occurs.

2. The method for controlling a radiation image pickup apparatus according to claim 1, wherein the radiation image pickup apparatus further includes a storage unit for storing the end threshold value and a comparator for comparing the end threshold value stored in the storage unit with the value of the detection signal, wherein the first mode involves a first step of storing the end threshold value in the storage unit, and the second mode involves a second step of generating a signal used for controlling the end of irradiation using the comparator if, as a result of comparison performed by the comparator, the value of the signal output from the detection unit becomes lower than the end threshold value stored in the storage unit during a period of time during which irradiation is applied to the pixel array in which the switch elements of the pixels are set in the non-conducting state by the drive circuit after the first mode occurs.

3. The method for controlling a radiation image pickup apparatus according to claim 2, wherein in the second step, the drive circuit sequentially sets the switch elements of the plurality of pixels in the conducting state on a row-by-row basis after a predetermined period of time has elapsed since determination of the end of irradiation.

4. The method for controlling a radiation image pickup apparatus according to claim 3, wherein the predetermined period of time is calculated on the basis of the signal output from the detection unit in the first mode.

5. The method for controlling a radiation image pickup apparatus according to claim 2, further comprising:

calculating a start threshold value used for detecting start of irradiation of the pixel array on the basis of a signal output from the detection unit during a period of time during which irradiation is not applied to the pixel array in which the switch elements of the pixels are sequentially set in the conducting state on a row-by-row basis by the drive circuit and a signal output from the detection unit during a period of time during which irradiation is performed on the pixel array in which the switch elements of the pixels are set in the non-conducting state by the drive circuit;

storing the start threshold value in the storage unit; and generating, in the second step, a signal determining the start of irradiation using the comparator if, as a result of comparison performed by the comparator, the value of the signal output from the detection unit exceeds the start threshold value during a period of time during which the switch elements of the plurality of pixels are sequentially set in the conducting state by the drive circuit.

6. The method for controlling a radiation image pickup apparatus according to claim 5, wherein the first mode further involves calculating the start threshold value using a signal output from the detection unit during a period of time during which irradiation is applied to the pixel array in which the switch elements of the plurality of pixels are sequentially set in the conducting state on a row-by-row basis by the drive circuit, and wherein the end threshold value is lower than the start threshold value.

7. The method for controlling a radiation image pickup apparatus according to claim 2, wherein the radiation generating apparatus configured to emit radiation to the pixel array emits radiation under a plurality of irradiation conditions in the first mode, wherein the first step involves storing a plurality of the end threshold values calculated for the plurality of irradiation conditions in the storage unit in association with the irradiation conditions, and wherein the second step involves selecting, from among the plurality of the end threshold values, the end threshold value corresponding to the irradiation condition for irradiation of the pixel array in the second mode and generating a signal that determines end of irradiation on the basis of the selected end threshold value by using the comparator.

8. The method for controlling a radiation image pickup apparatus according to claim 2, wherein a plurality of radiation generating apparatuses each configured to emit radiation to the pixel array are provided, wherein the first step involves storing a plurality of end threshold values calculated for the radiation generating apparatuses in the storage unit in association with the radiation generating apparatuses, and wherein the second step involves selecting, from among the plurality of the end threshold values, the end threshold value corresponding to the radiation generating apparatus used in the second mode and generating a signal for determining end of irradiation on the basis of the selected end threshold value by using the comparator.

9. A method for controlling a radiation image pickup apparatus, the radiation image pickup apparatus controlling an operation performed by a pixel array having a plurality of pixels arranged in a matrix on the basis of a detection signal that varies with the intensity of irradiation of the pixel array and an end threshold value used for detecting end of irradiation of the pixel array, each of the pixels including a conversion element configured to convert radiation into an electric carrier and a switch element configured to accumulate the electric carrier in a non-conducting state and to transmit an electric signal according to the electric carrier to a readout circuit configured to read out an image signal based on the electric signal in a conducting state, the method comprising:

calculating the end threshold value using a mode in which the end threshold value is calculated on the basis of the detection signal obtained during a period of time during which the switch elements of the plurality of pixels are set in a non-conducting state and radiation is emitted onto the pixel array.

10. A radiation image pickup apparatus comprising:

a pixel array having a plurality of pixels arranged in a matrix, each of the pixels including a conversion element configured to convert radiation into an electric carrier and a switch element configured to accumulate the electric carrier in a non-conducting state and to transmit an electric signal according to the electric carrier in a conducting state;

a drive circuit configured to control the switch element between a conducting state and a non-conducting state;

a readout circuit configured to read out an image signal based on the electric signal;

a detection unit configured to output a signal varying with an intensity of irradiation of the pixel array; and an arithmetic unit configured to calculate an end threshold value used for detecting end of irradiation on the basis of the signal output from the detection unit during a period of time during which irradiation is applied to the pixel array in which the switch elements of the plurality of pixels are set in the non-conducting state by the drive circuit.

11. The radiation image pickup apparatus according to claim 10, further comprising:

a control unit configured to control the drive circuit, the readout circuit, and the arithmetic unit, wherein the control unit controls the drive circuit, the readout circuit, and the arithmetic unit so as to switch between a first mode in which the arithmetic unit calculates the end threshold value and a second mode in which the switch element sequentially sets the switch elements of the plurality of pixels of the pixel array onto which radiation is emitted in a conducting state so that the switch elements of the pixels transfer the electric signal and the readout circuit reads the image signal based on the transferred electric signal.

12. The radiation image pickup apparatus according to claim 11, wherein the arithmetic unit includes a calculator configured to calculate the end threshold value by performing a computing process based on a signal output from the detection unit during a period of time during which irradiation is applied to the pixel array in which the switch elements of the plurality of pixels are set in the non-conducting state by the drive circuit in the first mode, a storage unit configured to store the end threshold value output from the calculator, and a comparator configured to compare a value of the signal output from the detection unit in the second mode with the end threshold value stored in the storage unit and output a signal that determines end of irradiation to the control unit.

13. The radiation image pickup apparatus according to claim 12, wherein the comparator outputs a signal that determines the end of irradiation to the control unit if a signal output from the detection unit is lower than the end threshold value in the second mode, and wherein upon receiving the signal that determines the end of irradiation from the comparator, the control unit controls the drive circuit so that the drive circuit sequentially set the switch elements of the pixels in the conducting state on a row-by-row basis.

14. The radiation image pickup apparatus according to claim 13, wherein the control unit controls the drive circuit so that the drive circuit sequentially set the switch elements of the pixels in the conducting state on a row-by-row basis after a predetermined period of time has elapsed since reception of the signal that determines the end of irradiation from the comparator, and wherein the predetermined period of time is calculated by the calculator on the basis of a signal output from the detection unit during a period of time during which irradiation is applied to the pixel array in which the switch elements of the pixels are set in the non-conducting state by the drive circuit and is stored in the storage unit.

15. The radiation image pickup apparatus according to claim 10, wherein
the arithmetic unit further calculates a start threshold value used for detecting the start of irradiation on the basis of the signal output from the detection unit during a period of time during which irradiation is not applied to the pixel array in which the switch elements of the plurality of pixels are sequentially set in the conducting state on a row-by-row basis by the drive circuit and the signal output from the detection unit during a period of time during which irradiation is applied to the pixel array in which the switch elements of the plurality of pixels are set in the non-conducting state by the drive circuit.

16. The radiation image pickup apparatus according to claim 15, wherein
the arithmetic unit performs an arithmetic process to calculate the start threshold value by further using a signal output from the detection unit during a period of time during which irradiation is applied to the pixel array in which the switch elements of the pixels are sequentially set in the conducting state on a row-by-row basis by the drive circuit.

17. The radiation image pickup apparatus according to claim 15, wherein
the end threshold value is lower than the start threshold value.

18. The radiation image pickup apparatus according to claim 12, wherein
a radiation generating apparatus configured to emit radiation onto the pixel array is capable of emitting radiation under a plurality of irradiation conditions,
wherein the calculator calculates a plurality of the end threshold values each corresponding to one of the irradiation conditions in the first mode,
wherein the storage unit stores each of the end threshold values in association with the corresponding one of the irradiation conditions, and
wherein the comparator determines end of irradiation on the basis of the end threshold value that is selected from among the end threshold values stored in the storage unit and that corresponds to the irradiation condition set in the second mode.

19. The radiation image pickup apparatus according to claim 12, wherein
a plurality of the radiation generating apparatuses that emit radiation onto the pixel array are provided,
wherein the calculator calculates a plurality of the end threshold values for the plurality of radiation generating apparatuses in the first mode,
wherein the storage unit stores the plurality of end threshold values in association with the radiation generating apparatuses, and
wherein the comparator determines end of irradiation on the basis of the end threshold value that is selected from among the end threshold values stored in the storage unit and that corresponds to the radiation generating apparatus used in the second mode.

20. A radiation image pickup system comprising:
the radiation image pickup apparatus according to claim 10; and
the radiation generating apparatus.

* * * * *